US010682359B2

(12) United States Patent
D'Antonio

(10) Patent No.: US 10,682,359 B2
(45) Date of Patent: Jun. 16, 2020

(54) INHIBITORS OF GLUCOSE KINASES, ALONG WITH METHODS OF THEIR FORMATION AND USE

(71) Applicant: University of South Carolina, Columbia, SC (US)

(72) Inventor: Edward L. D'Antonio, Bluffton, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/939,952

(22) Filed: Mar. 29, 2018

(65) Prior Publication Data

US 2018/0280404 A1    Oct. 4, 2018

Related U.S. Application Data

(60) Provisional application No. 62/479,469, filed on Mar. 31, 2017.

(51) Int. Cl.

| | | |
|---|---|---|
| *A61K 31/352* | (2006.01) | |
| *A61K 31/5377* | (2006.01) | |
| *A61K 31/18* | (2006.01) | |
| *A61K 31/515* | (2006.01) | |
| *A61K 31/4545* | (2006.01) | |
| *A61K 31/519* | (2006.01) | |
| *A61P 33/00* | (2006.01) | |
| *A61K 31/4162* | (2006.01) | |
| *A61K 31/4439* | (2006.01) | |
| *A61K 31/473* | (2006.01) | |
| *A61K 31/444* | (2006.01) | |
| *A61K 31/381* | (2006.01) | |
| *A61K 31/357* | (2006.01) | |

(52) U.S. Cl.
CPC .......... *A61K 31/5377* (2013.01); *A61K 31/18* (2013.01); *A61K 31/352* (2013.01); *A61K 31/357* (2013.01); *A61K 31/381* (2013.01); *A61K 31/4162* (2013.01); *A61K 31/444* (2013.01); *A61K 31/4439* (2013.01); *A61K 31/4545* (2013.01); *A61K 31/473* (2013.01); *A61K 31/515* (2013.01); *A61K 31/519* (2013.01); *A61P 33/00* (2018.01); *Y02A 50/414* (2018.01)

(58) Field of Classification Search
CPC .................................................. A61K 31/352
See application file for complete search history.

(56) References Cited

U.S. PATENT DOCUMENTS

| | | | |
|---|---|---|---|
| 4,761,404 A | 8/1988 | Bugianesi et al. | |
| 5,763,470 A * | 6/1998 | Tang | A61K 31/352 |
| | | | 514/406 |
| 6,551,600 B2 | 4/2003 | Hawkins et al. | |
| 6,723,710 B2 | 4/2004 | Christianson et al. | |
| 8,618,080 B2 | 12/2013 | Bauer et al. | |
| 9,956,240 B2 | 5/2018 | D'Antonio et al. | |
| 2017/0145042 A1 | 5/2017 | D'Antonio | |
| 2018/0155373 A1 | 6/2018 | D'Antonio | |

FOREIGN PATENT DOCUMENTS

WO    WO/0035944    6/2000

OTHER PUBLICATIONS

Habib et al. Tetrahedron, 2009, vol. 65, pp. 5799-5804 (Year: 2009).*
Ito et al. Life Sciences, 2017, vol. 180, pp. 137-142 (Published Online May 17, 2017) (Year: 2017).*
Mao et al. Blood, Nov. 16, 2008, vol. 112, No. 11, p. 568-569 (Abstract Attached) (Year: 2008).*
Yin et al. Bioorganic & Medicinal Chemistry Letters, 2013, vol. 23, pp. 3314-3319 (Year: 2013).*
Rahmani-Nezhad et al. European Journal of Medicinal Chemistry, 2014, vol. 86, pp. 562-569 (Year: 2014).*
Calamini et al. Nature Chemical Biology, Feb. 2012, vol. 8, pp. 185-196 (Year: 2012).*
Gallo-Ebert et al. Antimicrobial Agent and Chemotherapy, Jan. 2014, vol. 58, No. 1, pp. 258-266 (Year: 2014).*
Fatome et al. European Journal of Medicinal Chemistry—Chimica Theapeutica, Jan.-Feb. 1976, vol. 11, No. 1, pp. 81-82 (Year: 1976).*
D'Abusco, et al. "A peptidyl-glucosamine derivative affects IKKα kinase activity in human chondrocytes," *Arthritis Research & Therapy*, 12:R18, (2010), pp. 1-11.
Doerig, Christian. "Protein kinases as targets for anti-parasitic chemotherapy," *Biochimica et Biophysica Acta* 1697, (2004), pp. 155-168.
Heussler, et al. "Hijacking of Host Cell IKK Signalosomes by the Transforming Parasite *Theileria*", *Science*, 298, 2002, pp. 1033-1036.
Lefebvre, et al. "Mononucleoside phosphotriester derivatives with S-acyl-2-thioethyl bioreversible phosphate-protecting groups: Intracellular delivery of 3'-azido-2',3'-dideoxythymidine 5'-monophosphate," *J. Med. Chem.* 38, (1995), pp. 3941-3950.
Ruda, et al. "Aryl phosphoramidates of 5-phospho erythronohydroxamic acid, a new class of potent trypanocidal compounds," *J. Med Chem.* 53, (2010), pp. 6071-6078.

(Continued)

*Primary Examiner* — James D. Anderson
(74) *Attorney, Agent, or Firm* — Dority & Manning, P.A.

(57) ABSTRACT

Compounds discovered through a high-throughput screen, along with methods of use of the compounds, are provided. The compounds can be used to strongly inhibit key drug targets found in protozoan parasites, e.g., the target *Trypanosoma cruzi* glucokinase. Compounds include derivatives of N-phenylbenzenesulfonamide, barbituric acid, (R)-3-(piperidin-2-yl)pyridine, 3-nitro-2-phenyl-2H-chromene, 6-amino-3-methyl-4-phenyl-1,4-dihydropryranole[2,3-c] pyrazole-5-carbonitrile, and gossypol (2,2'-Bis(formyl-1,6, 7-trihydroxy-5-isopropyl-3-methylnaphthalene).

10 Claims, 5 Drawing Sheets

(56) References Cited

OTHER PUBLICATIONS

Ruda, et al. "Synthesis and biological evaluation of phosphate prodrugs of 4-phospho-Derythronohydroxamic acid, an inhibitor of 6-phosphogluconate dehydrogenase," *ChemMedChem*, 2, (2007), pp. 1169-1180.

Stern, et al. "Structures of type B ribose 5-phosphate isomerase from Trypanosoma cruzi shed light on the determinants of sugar specificity in the structural family," *FEBS Journal*, 278, (2011), pp. 793-808.

Stern, et al. "Ribose 5-phosphate isomerase type B from Trypanosoma cruzi: kinetic properties and site-directed mutagenesis reveal information about the reaction mechanism," *Biochem. Journal*, 401, (2007), pp. 279-285.

Wilson, et al. "Sequencing, Modeling, and Selective Inhibition of *Trypanosoma brucei* Hexokinase," *Chemistry & Biology*, 9, (2002), pp. 839-847.

PCT International Search Report, dated Mar. 31, 2000.

* cited by examiner

US 10,682,359 B2

INHIBITORS OF GLUCOSE KINASES, ALONG WITH METHODS OF THEIR FORMATION AND USE

CROSS REFERENCE TO RELATED APPLICATION

This application claims filing benefit of U.S. Provisional Patent Application Ser. No. 62/479,469 having a filing date of Mar. 31, 2017, which is incorporated herein by reference for all purposes.

BACKGROUND

Kinetoplastid parasites, such as *Trypanosome cruzi* (*T. cruzi*), *Trypanosoma brucei* (*T. brucei*), and *Leishmania* spp., utilize and depend on the pentose phosphate pathway (PPP) for the reducing agent NADPH and also rely on the PPP for support for nucleic acid and nucleotide biosynthesis. The PPP is essential for these organisms and obstruction of the pathway leads to cell death and can be caused by inhibition of the enzyme, glucose 6-phosphate dehydrogenase, for instance by use of a drug. In order to create a therapeutic drug, an inhibitor should selectively block the parasite homologue and avoid cross-reactivity with the human homologue (i.e., bind weaker or not bind at all), giving rise to a good selectively ratio.

*T. cruzi* is the causative agent for Chagas' disease and benznidazole and nifurtimox are the two main clinically available treatments available in Latin America. These drugs have the potential for resistance because they were developed over 35 years ago and alternative drugs have not emerged. *T. brucei* is the causative agent for human African sleeping sickness and various drugs are available, such as pentamidine, suramin, eflornithine, and melarsoprol. *Leishmania* spp. are protozoan parasites causing Leishmaniasis and medical intervention requires treatment such as pentavalent antimony-based medicines, or more expensive treatments such as amphotericin B, miltefosine, or paramomycin. The drugs for these kinetoplasid diseases all require substantial improvements in their tolerability, safety, and efficacy.

A need exists for new drugs that strongly bind to drug targets found in these parasites. Such a need includes inhibitors of the glucose kinase enzymes, hexokinase and glucokinase. A need also exists for such inhibitors that will provide an alternative to the clinically used drugs at the present time.

SUMMARY

Objects and advantages of the invention will be set forth in part in the following description, or may be obvious from the description, or may be learned through practice of the invention.

Compounds are generally provided, along with pharmaceutical compositions including such compounds. Compounds disclosed include derivatives of scaffolds based upon N-phenylbenzenesulfonamide, barbituric acid, (R)-3-(piperidin-2-yl)pyridine, 3-nitro-2-phenyl-2H-chromene, 6-amino-3-methyl-4-phenyl-1,4-dihydropryranole[2,3-c] pyrazole-5-carbonitrile, and gossypol (2,2'-Bis(formyl-1,6, 7-trihydroxy-5-isopropyl-3-methylnaphthalene), among other individual compounds as described further herein.

Methods are also generally provided for inhibiting glucose kinase enzymes, hexokinase and glucokinase, such as via administering to the human the pharmaceutical composition that includes such a compound.

Methods are also generally provided for treating a mammal that is infected by a parasitic organism, such as via administering to the mammal the pharmaceutical composition that includes such a compound.

Other features and aspects of the present invention are discussed in greater detail below.

BRIEF DESCRIPTION OF THE DRAWINGS

FIG. 4 shows $IC_{50}$ curves (enzyme—inhibitor affinity) for TcGlcK inhibition studies of four compounds: (a) 4b, (b) 4a, (c) 6a, and (d) 1a.

FIG. 5 shows a dose response of compound activity on the in vitro *T. cruzi* (Tulahuen strain) intracellular infective form (amastigote and trypomastigote life stages) inhibition in NIH-3T3 fibroblasts of four compounds: (a) 4b, (b) 4a, (c) 6a, and (d) 1a.

DEFINITIONS

Figure 1:
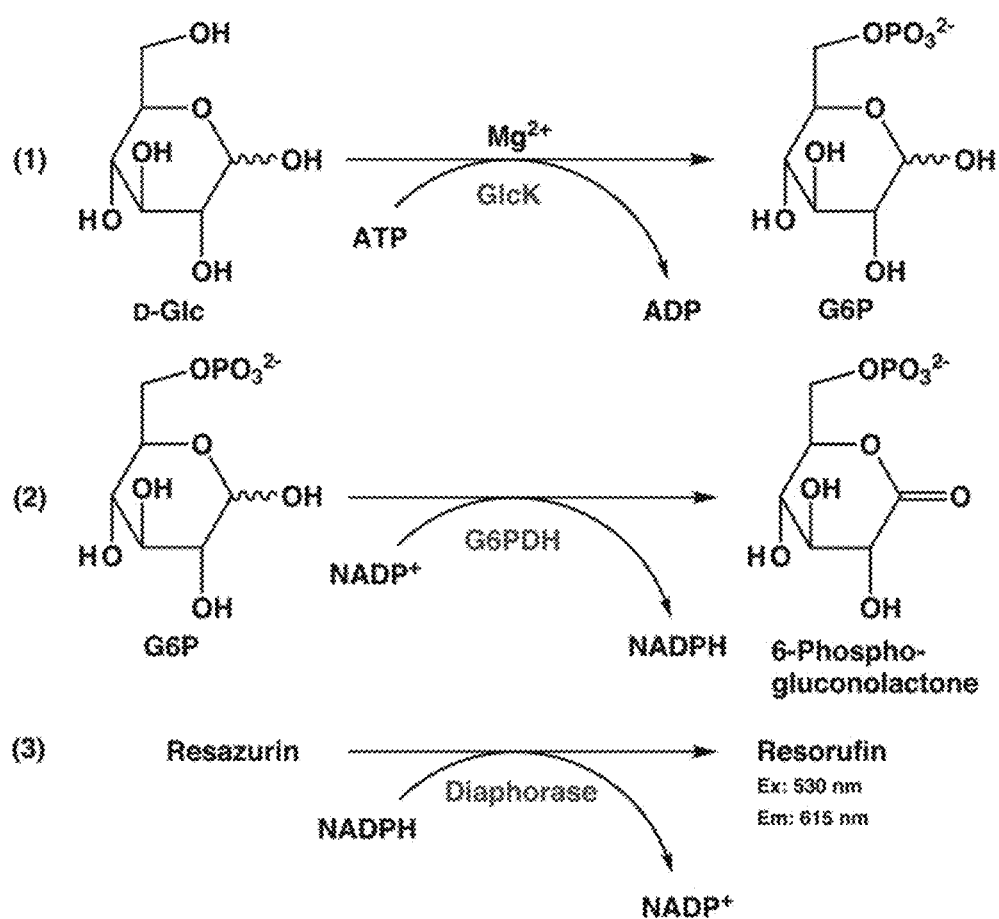
FIG. 1 schematically illustrates a high-throughput screening (HTS) assay representing a *Trypanosoma cruzi* glucokinase (TcGlcK)—*Homo sapiens* glucose-6-phosphate dehydrogenase sequence (HsΔG6PDH)—diaphorase enzyme coupled assay. Compounds from screening libraries were screened at a concentration of 20 μM and the endpoint used was resorufin, which has fluorescence excitation and emission wavelengths of 530 nm and 615 nm, respectively.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "related compounds thereof" refers to compounds that have the basic structure of the base compound with substituted atom(s) and/or substituted side groups, while still keeping the functionality of the base compound.

The term "pharmaceutically effective amount" refers to the amount of a drug or pharmaceutical agent that will elicit the biological or medical response of a tissue, system, animal, or human that is being sought by a researcher or clinician. This amount can be a therapeutically effective amount.

The term "pharmaceutically acceptable carrier" is used herein to refer to a carrier that is useful in preparing a pharmaceutical composition that is generally safe, non-toxic and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable" it is meant the carrier must be compatible with the other ingredients of the formulation and not deleterious to the recipient thereof.

The terms "administration of" or "administering a" pharmaceutical composition should be understood to mean providing a pharmaceutical composition to an individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "treatment" or "treating" means any administration of a pharmaceutical composition to obtain a desired pharmacologic and/or physiologic effect. The effect may be prophylactic in terms of completely or partially preventing a disease or symptom thereof, and/or may be therapeutic in terms of a partial or complete cure for a disease and/or adverse effect attributable to the disease. Treatment includes (a) inhibiting the disease in the subject that is experiencing or displaying the pathology or symptomatology of the diseased (i.e., arresting further development of the pathology and/or symptomatology), or (b) ameliorating the disease in the subject that is experiencing or displaying the pathology or symptomatology of the diseased (i.e., reversing the pathology and/or symptomatology).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Compounds and methods are generally provided that can be used against certain drug-targets, e.g., *Trypanosoma cruzi* glucokinase (TcGlcK), that are found in protozoan parasites. The compounds may serve as viable substitutes for currently used drugs in clinical settings. The compounds described herein include experimentally confirmed potent inhibitors of *T. cruzi* glucokinase, and may also be potent inhibitors of *T. cruzi* hexokinase and/or *Leishmania* species (e.g., *Leishmania braziliensis*). The drug compounds described herein may offer an alternative to the mainstream drugs that are used in the clinic for three diseases of the trypanosome, such as American Trypanosomiasis (Chagas' disease), Human African Trypanosomiasis (Human African Sleeping Sickness), and Leishmaniasis caused by parasites *T. cruzi, T. brucei*, and *Leishmania* spp., respectively.

From a high-throughput screen (HTS) of *Trypanosoma cruzi* glucokinase (TcGlcK) using 13,040 compounds from two screening libraries of small-molecules and natural products, 44 confirmed hits were identified. Of these 44 hit compounds, several unique chemical scaffolds were realized as well as multiple compounds that are not tied to the identified scaffolds. The identified scaffolds include derivatives of scaffolds based upon N-phenylbenzenesulfonamide, barbituric acid, (R)-3-(piperidin-2-yl)pyridine, 3-nitro-2-phenyl-2H-chromene, 6-amino-3-methyl-4-phenyl-1,4-dihydropryranole[2,3-c]pyrazole-5-carbonitrile, and gossypol (2,2'-Bis(formyl-1,6,7-trihydroxy-5-isopropyl-3-methyl-naphthalene), including racemates of the derivatives.

I. Scaffold 1-N-phenylbenzenesulfonamide

Inhibitors referred to herein as Scaffold 1 inhibitors are based upon N-phenylbenzenesulfonamide, which has the following structure:

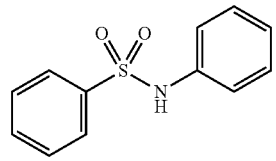 [SMILES: O=S(=O)(Nc1ccccc1)c1ccccc1]

Scaffold 1 inhibitors can generally have the following structure:

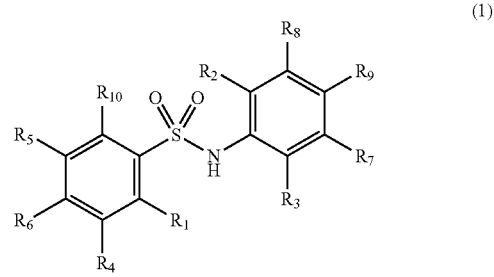

(1)

in which $R_1$ to $R_{10}$ are independently selected from hydrogen, halogen, C1-C4 alkyl, C1-C4 alkoxy, methyl sulfide, or any two adjacent of which are components of a ring fused to the respective aryl group including conjugated and non-conjugated rings, including heterocyclic rings and derivatized rings derivatized with one or more of halogen, C1-C4 alkyl, C1-C4 alkoxy, and methyl sulfide.

In one embodiment, Scaffold 1 inhibitors can include those of the above structure in which:

$R_1$, $R_2$, $R_5$ are independently selected from hydrogen or halogen;

$R_3$, $R_4$, $R_5$, $R_6$, $R_{10}$ are independently selected from hydrogen, halogen, methyl, methoxy, or ethoxy; and $R_7$, $R_9$ are independently selected from hydrogen, halogen, hydroxyl, methoxy, methyl sulfide, or are components of a conjugated ring fused to the respective aryl group.

Specific examples of Scaffold 1 inhibitors include the following:

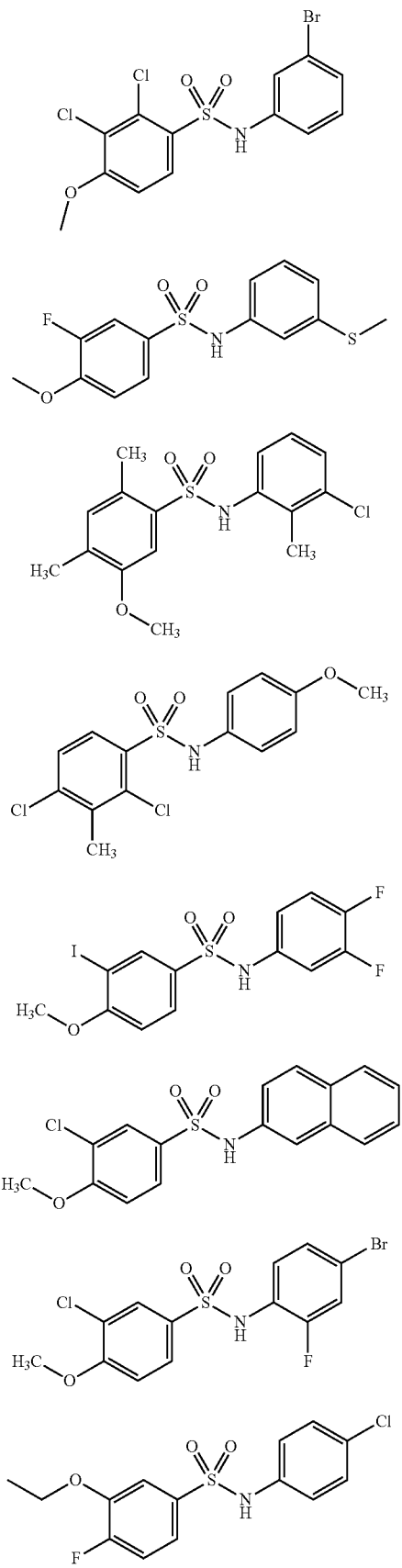
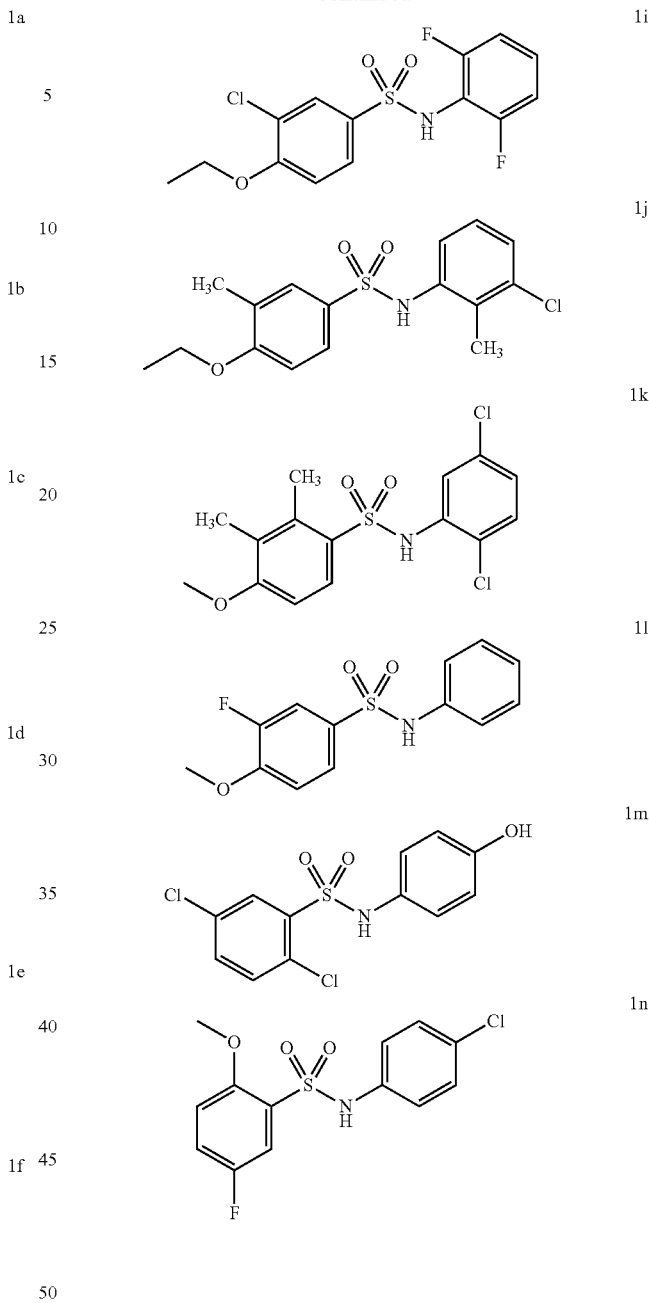
II. Scaffold 2—Barbituric Acid
Inhibitors referred to herein as Scaffold 2 inhibitors are based upon barbituric acid, which has the following structure:
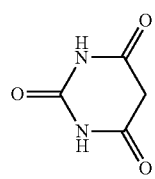
Scaffold 2 inhibitors can generally have the following structure:

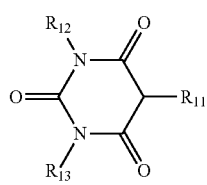

(2)

in which $R_{11}$ is hydrogen, C1-C6 alkyl, optionally substituted with conjugated and/or non-conjugated rings, including heterocyclic rings and fused ring systems that can include derivatized rings derivatized with one or more of hydrogen, halogen, C1-C6 alkyl, C1-C6 alkoxy. For instance, in one embodiment $R_{11}$ can be hydrogen, C1-C6 alkyl, or C1-C6 alkyl substituted with one or more rings, wherein the one or more rings include conjugated rings, non-conjugated rings, heterocyclic rings, or any combination thereof, and wherein the rings are optionally derivatized with one or more of hydrogen, halogen, C1-C6 alkyl, C1-C6 alkoxy, or amine $R_{12}$ and $R_{13}$ are independently hydrogen, C1-C6 alkyl, C1-C6 alkoxy, and can include conjugated or non-conjugated rings, including heterocyclic rings and fused ring systems and can include derivatized rings derivatized with one or more of hydrogen, halogen, C1-C6 alkyl, C1-C6 alkoxy.

In one embodiment, Scaffold 2 inhibitors can include those of the above structure in which:

$R_{11}$ is hydrogen or =C—$R_{14}$ in which $R_{14}$ is a substituted or unsubstituted C5 or C6 conjugated ring system. For instance, $R_{14}$ can include one or more conjugated rings, non-conjugated rings, heterocyclic rings, or any combination thereof, and optionally the rings can be derivatized with one or more of halogen, C1-C6 alkyl, C1-C6 alkoxy, or amine. In addition, $R_{12}$ and $R_{13}$ can be independently hydrogen, methyl, or can include a conjugated or non-conjugated ring system, including fused ring systems. For instance, $R_{12}$ and $R_{13}$ can include one or more rings, and the rings can include conjugated rings, non-conjugated rings, heterocyclic rings, or any combination thereof, and the rings can optionally be derivatized with one or more of hydrogen, halogen, C1-C6 alkyl, or C1-C6 alkoxy.

For example, in one embodiment $R_{14}$ can have the following structure:

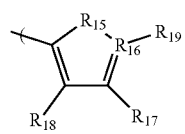

in which $R_{15}$, is O, N or S, $R_{16}$ is O, N, or S, and $R_{17}$, $R_{18}$, $R_{19}$ are independently hydrogen, halogen, or a conjugated or non-conjugated ring system, including fused ring systems.

In one embodiment, $R_{14}$ can have the following structure:

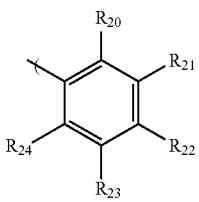

in which $R_{20}$, $R_{21}$, $R_{22}$, $R_{23}$, $R_{24}$ are independently primary, secondary or tertiary amine (including, e.g., alkyl amine, cycloalkyl amine, heterocycloalkyl amine), C1-C4 alkyl, C1-C4 alkoxy, halogen, hydroxyl, or any two adjacent of which are components of a ring fused to the aryl group. For instance, a ring fused to the aryl group can include a conjugated ring, a non-conjugated ring, and a ring can be a heterocyclic ring.

Specific examples of inhibitors based on Scaffold 2 include the following:

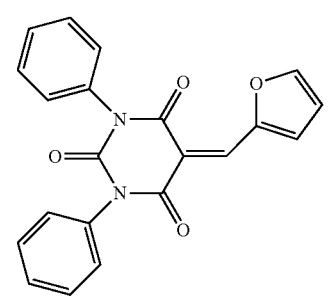

2a

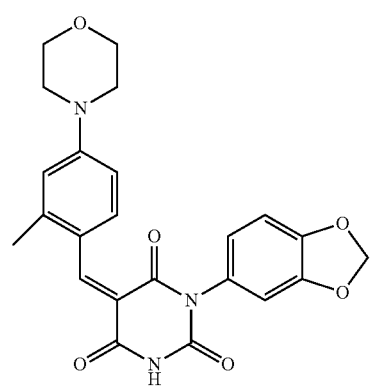

2b

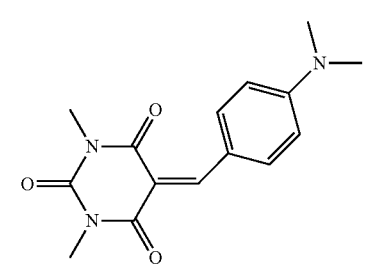

2c

-continued

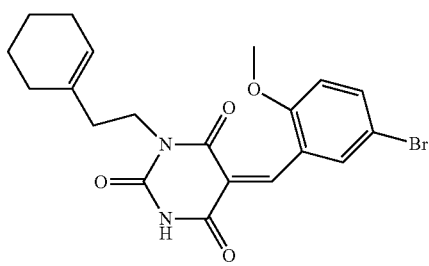
2d

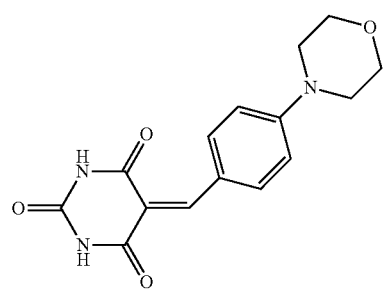
2e

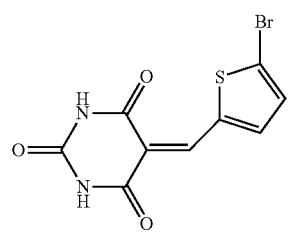
2f

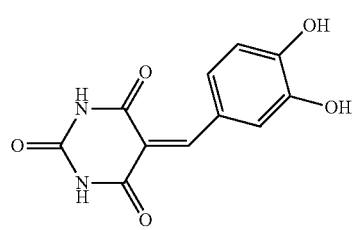
2g

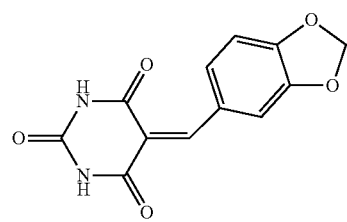
2h

III. Scaffold 3-(R)-3-(Piperidin-2-yl)pyridine

Inhibitors referred to herein as Scaffold 3 inhibitors are based upon (R)-3-(Piperidin-2-yl)pyridine which has the following structure:

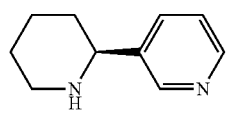 [SMILES: c1cncc([C@@H]2CCCCN2)c1]

Scaffold 3 inhibitors can generally have the following structure:

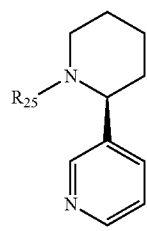
(3)

in which $R_{25}$ is a fused ring system or a substituted or unsubstituted C1-C10 alkyl or alkoxy, optionally substituted with conjugated or non-conjugated rings, including heterocyclic rings and fused ring systems that can include derivatized rings derivatized with one or more of hydrogen, halogen, C1-C4 alkyl, or C1-C4 alkoxy.

By way of example, in one embodiment, $R_{25}$ can be selected from one of the following:

3a

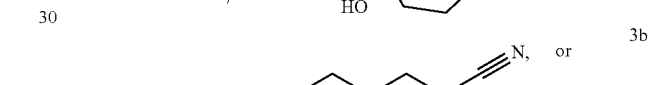
3b

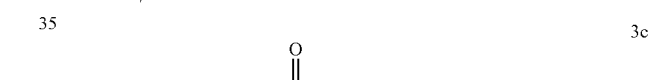
3c

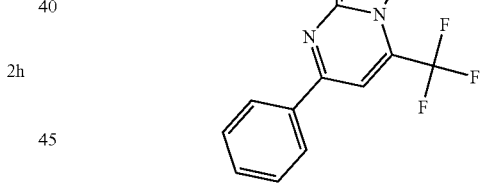

IV. Scaffold 4—3-nitro-2-phenyl-2H-chromene

Inhibitors referred to herein as Scaffold 4 inhibitors are based upon 3-nitro-2-phenyl-2H-chromene, which has the following structure:

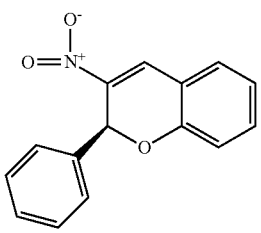 [SMILES: O=[N+]([O-])C1=Cc2ccccc2O[C@H]1c1ccccc1]

Scaffold 4 inhibitors can generally have the following structure:

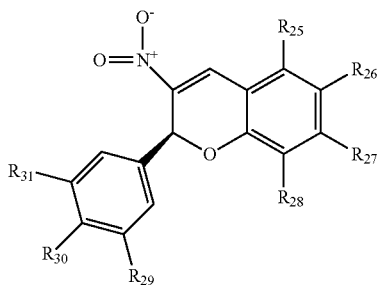
(4)

in which $R_{25}$, $R_{26}$, $R_{27}$, $R_{28}$, $R_{29}$, $R_{30}$, $R_{31}$ are independently selected from hydrogen, halogen C1-C4 alkyl, C1-C4 alkoxy, or any two adjacent of which are components of a ring fused to the respective aryl group including conjugated and non-conjugated rings, including heterocyclic rings and derivatized rings derivatized with one or more of hydrogen, halogen, C1-C4 alkyl, C1-C4 alkoxy.

In one embodiment, Scaffold 4 inhibitors can include those of the above structure in which:

$R_{25}$, $R_{26}$, $R_{27}$, $R_{28}$, are independently selected from hydrogen, halogen, or any two adjacent of which are components of a conjugated ring fused to the aryl group, and $R_{29}$, $R_{30}$, $R_{31}$ are independently selected from hydrogen, C1-C4 alkoxy, or any two adjacent of which are components of a conjugated or non-conjugated ring fused to the aryl group in which the ring can optionally be a heterocyclic ring.

Specific examples of Scaffold 4 inhibitors include the following:

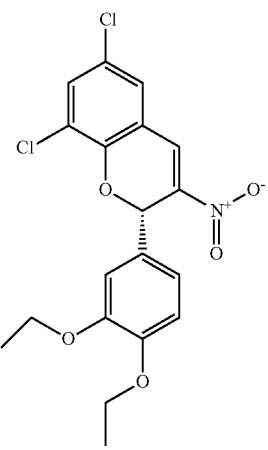
4a

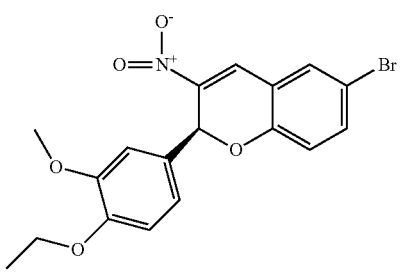
4b

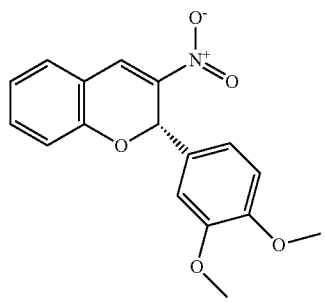
4c

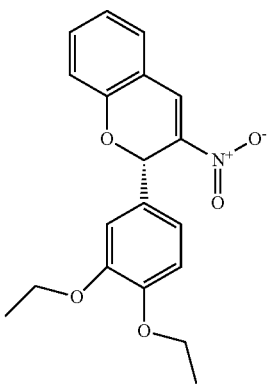
4d

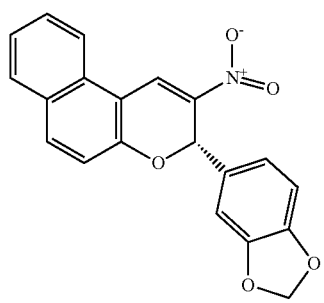
4e

V. Scaffold 5—6-amino-3-methyl-4-phenyl-1,4-dihydropyrano[2,3-c]pyrazole-5-carbonitrile Inhibitors referred to herein as Scaffold 5 inhibitors are based upon 6-amino-3-methyl-4-phenyl-1,4-dihydropyrano[2,3-c]pyrazole-5-carbonitrile, which has the following structure:

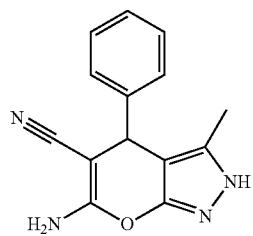 [SMILES: Cc1[nH]nc2c1C(c1ccccc1)C(C#N)=C(N)O2]

Scaffold 5 inhibitors can generally have the following structure:

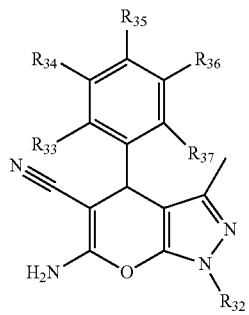
(5)

in which

R$_{32}$, when present, is hydrogen or a conjugated or non-conjugated ring, including heterocyclic rings and derivatized rings derivatized with one or more of halogen, C1-C4 alkyl, C1-C4 alkoxy; and R$_{33}$, R$_{34}$, R$_{35}$, R$_{36}$, R$_{37}$ are independently hydrogen, halogen, C1-C4 alkyl, C1-C4 alkoxy, or NO$_2^-$.

In one embodiment, Scaffold 5 inhibitors can include those of the above structure in which:

R$_{32}$ is hydrogen a conjugated optionally halogenated and/or methylated, and

R$_{33}$, R$_{34}$, R$_{35}$, R$_{36}$, R$_{37}$ are independently selected from hydrogen, halogen, C1-C4 alkyl, C1-C4 alkoxy, NO$_2^-$.

Specific examples of Scaffold 5 inhibitors include the following:

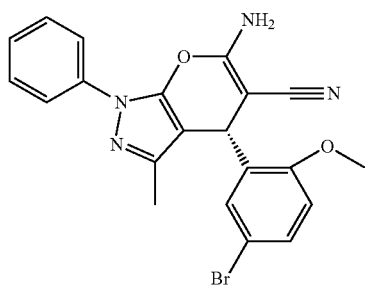
5a

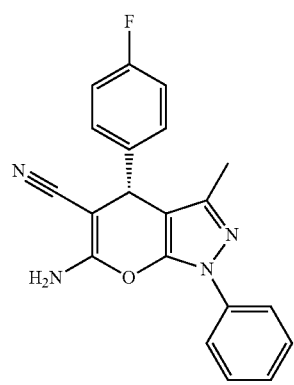
5b

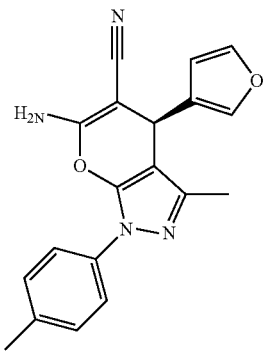
5c

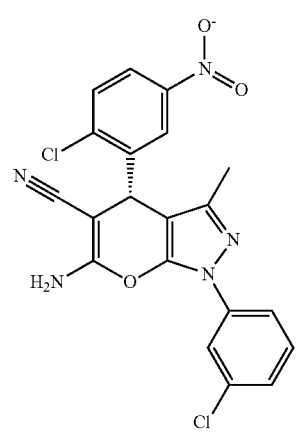
5d

VI. Scaffold 6-Gossypol (2,2'-Bis(formyl-1,6,7-trihydroxy-5-isopropyl-3-methylnaphthalene)

Inhibitors referred to herein as Scaffold 6 inhibitors are based upon gossypol, which has the following structure:

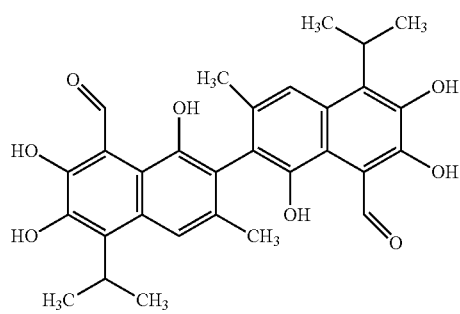 [SMILES: Cc1cc2c(C(C)C)c(O)c(O)c(C=O)c2c(O)c1-c1c(C)cc2c(C(C)C)c(O)c(O)c(C=O)c2c1O]

Scaffold 6 inhibitors can generally have the following structure:
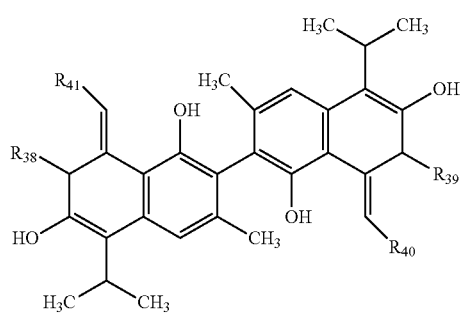
(6)
in which
R$_{38}$, R$_{39}$ are independently =O or OH; and
R$_{40}$ and R$_{41}$ are independently O, or one of the following:
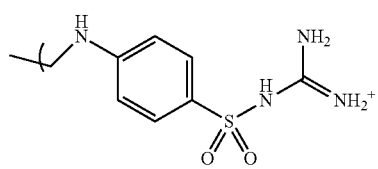
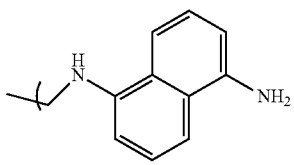
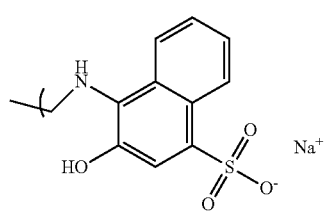
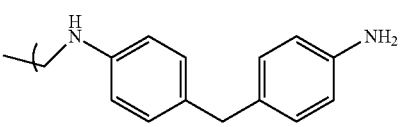
Specific examples of Scaffold 6 inhibitors include the following:
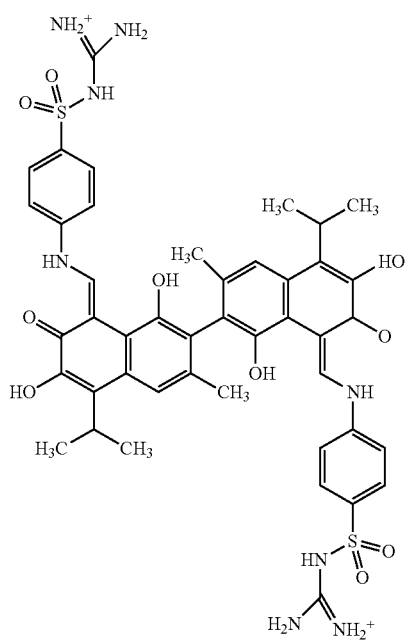
6a
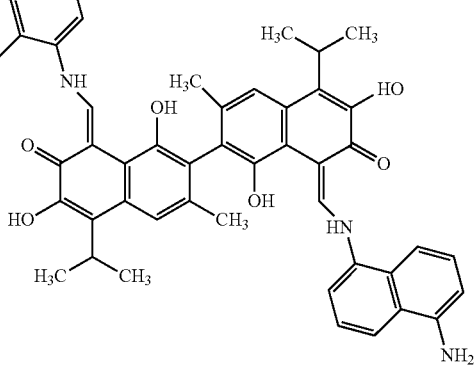
6b -continued
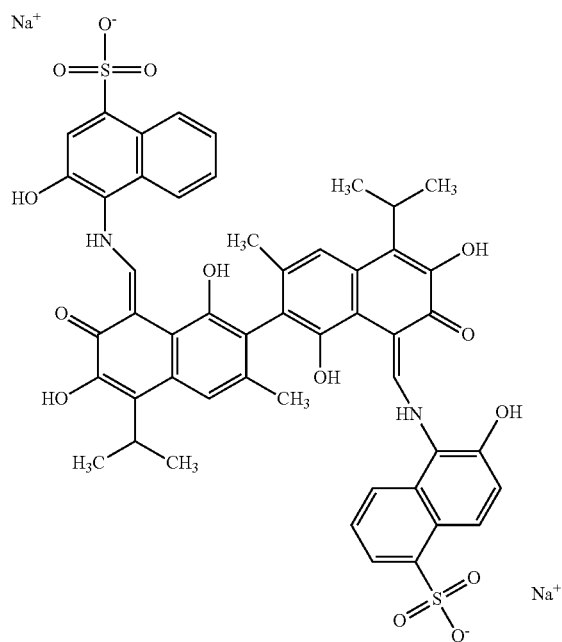
6c
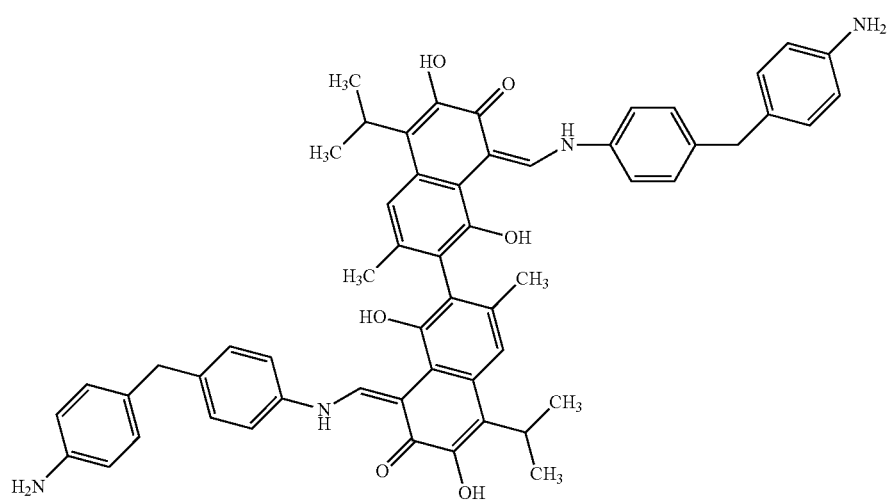
6d
VI. Singleton Inhibitors
Several singleton inhibitors are also disclosed herein, having the following structures:
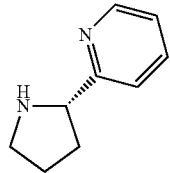
(7)
-continued
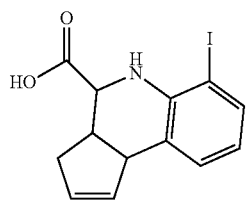
(8)

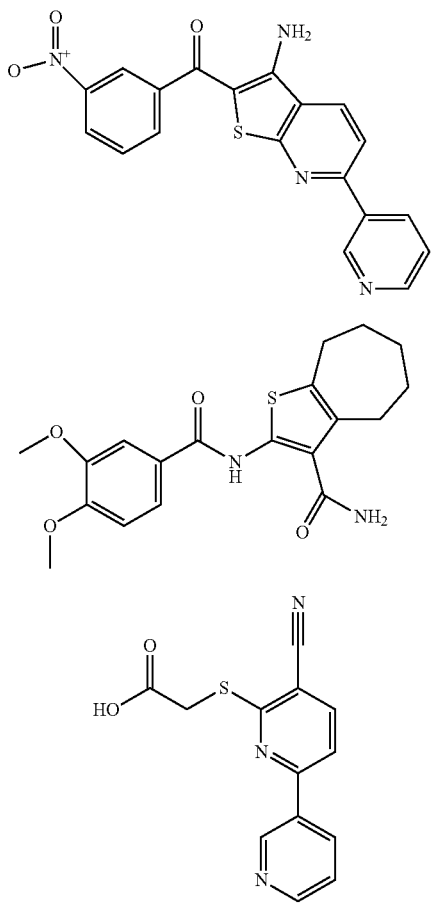

VIII. Pharmaceutical Compositions

Pharmaceutical compositions are provided that include a pharmaceutically acceptable carrier and at least one compound as disclosed herein, and in one embodiment, one of the 44 compounds illustrated above, i.e., a compound having any one of the structures 1a-1n, 2a-2h, 3a-3c, 4a-4e, 5a-5c, 6a-6d, 7, 8, 9, 10, or 11.

Pharmaceutical compositions may be prepared by any of the methods well known in the art of pharmacy. Pharmaceutical compositions encompass any compositions made by admixing the active ingredients and a pharmaceutically acceptable carrier. The carrier may take a wide variety of forms depending on the form of preparation desired for administration, e.g., oral or parenteral (including intravenous). Thus, the pharmaceutical composition can be presented as discrete units suitable for oral administration such as capsules, cachets, or tablets each containing a predetermined amount of the active ingredients. Further, the composition can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the composition may also be administered by controlled release means and/or delivery devices. The foregoing list is illustrative only and is not intended to be limiting in any way.

Pharmaceutical compositions intended for oral use may contain one or more agents selected from the group consisting of sweetening agents, flavoring agents, coloring agents and preserving agents in order to provide pharmaceutically elegant and palatable preparations. Tablets may contain a composition having at least one of the compounds described herein in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. A tablet may be prepared by compression or molding, optionally with one or more accessory ingredients or adjuvants. Compressed tablets may be prepared by compressing, in a suitable machine, at least one of disclosed compounds in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions for oral use may also be presented as hard gelatin capsules wherein one or more of the disclosed compounds is mixed with an inert solid diluent, for example, calcium carbonate, calcium phosphate or kaolin, or as soft gelatin capsules wherein the compound(s) is/are mixed with water or an oil medium, for example peanut oil, liquid paraffin, or olive oil.

Pharmaceutical compositions can also include aqueous suspensions, which contain the active materials in admixture with excipients suitable for the manufacture of aqueous suspensions. In addition, oily suspensions may be formulated by suspending at least one of the disclosed compounds in a vegetable oil, for example arachis oil, olive oil, sesame oil or coconut oil, or in a mineral oil such as liquid paraffin. Oily suspensions may also contain various excipients. The pharmaceutical composition may also be in the form of oil-in-water emulsions, which may also contain excipients such as sweetening and flavoring agents.

Pharmaceutical compositions can be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment can be prepared by mixing hydrophilic material and water, together with about 5 wt % to about 10 wt % of one or more of the disclosed compound, to produce a cream or ointment having a desired consistency.

Pharmaceutical compositions can also be in a form suitable for rectal administration wherein the carrier is a solid. Suitable carriers include cocoa butter and other materials commonly used in the art.

IX. Methods of Inhibiting Glucokinase and/or Hexokinase

Methods are also provided for inhibiting glucokinase and/or hexokinase, both in vitro and in vivo. In one embodiment, the method comprises contacting the glucokinase and/or hexokinase with at least one of the disclosed compounds, and in one embodiment, one of the 44 compounds illustrated above, i.e., a compound having one of structures 1a-1n, 2a-2h, 3a-3c, 4a-4e, 5a-5c, 6a-6d, 7, 8, 9, 10, or 11.

For instance, a method is provided for inhibiting glucokinase and/or hexokinase in a parasitic organism. This method comprises administering to the human a composition comprising a pharmaceutically acceptable carrier and at least one compound having one of structures 1a-1n, 2a-2h, 3a-3c, 4a-4e, 5a-5c, 6a-6d, 7, 8, 9, 10, or 11. The parasitic organism can be of a disease associated by the parasite that contains glucokinase and/or hexokinase such diseases include American Trypanosomiasis (Chagas' disease), Human African Trypanosomiasis (African Sleeping Sickness), Leishmaniasis, Malaria, Schistosomaisis (Snail Fever), Filarial diseases, etc.

X. Methods of Treatment

Also, a method is provided for treating a mammal that is infected by a parasitic organism. This method comprises administering to the disease-affected mammal a composition comprising a pharmaceutically acceptable carrier and at least one compound having one of structures 1a-1n, 2a-2h, 3a-3c, 4a-4e, 5a-5c, 6a-6d, 7, 8, 9, 10, or 11. Examples of such disease-affected mammals include humans and domestic animals (e.g., dogs, cats, and thereof).

EXAMPLES

Experimental Procedures
Materials:

Triton X-100 was purchased from Serva (Heidelberg, Germany). Dulbecco's modified Eagle's medium (DMEM) was purchased from CellGro. Lysozyme, phenylmethylsulfonyl fluoride (PMSF), N-benzyl-2-nitro-1H-imidazole-1-acetamide (benznidazole, 97%), chlorophenol red β-D-galactoside (CPRG), imidazole, β-nicotinamide adenine dinucleotide phosphate hydrate (NADP+), adenosine 5'-triphosphate disodium salt hydrate (ATP), D-glucose-6-phosphate sodium salt (G6P), *Clostridium kluyveri* diaphorase (E.C. 1.8.1.4), resazurin sodium salt, kanamycin sulfate, and dimethyl sulfoxide (DMSO) were purchased from Sigma (St. Louis, Mo.). Nickel-nitrolotriacetic acid (Ni-NTA) resin was purchased from Invitrogen (Carlsbad, Calif.). Gel filtration chromatography was performed using the HiLoad Superdex 200 16/60 column from GE Healthcare (Pittsburgh, Pa.). The ZYM-5052 medium used for autoinduction in overexpression experimentation was prepared from tryptone, yeast extract, D-glucose, α-lactose, glycerol, magnesium sulfate, sodium phosphate dibasic, potassium phosphate monobasic, ammonium chloride, and sodium sulfate. These components and all other chemicals were purchased from Fisher Scientific (Hampton, N.H.).
Expression and Purification of Recombinant
TcGlcK and HsΔG6PDH:

Known Protocols were carried out for the overexpression and purification of *Trypanosome cruzi* glucokinase (TcGlcK) and a truncation mutant of *Homo sapiens* glucose-6-phosphate dehydrogenase (residues ranged from 29 to 511) and designated simply as "HsΔG6PDH".

Figure 2:
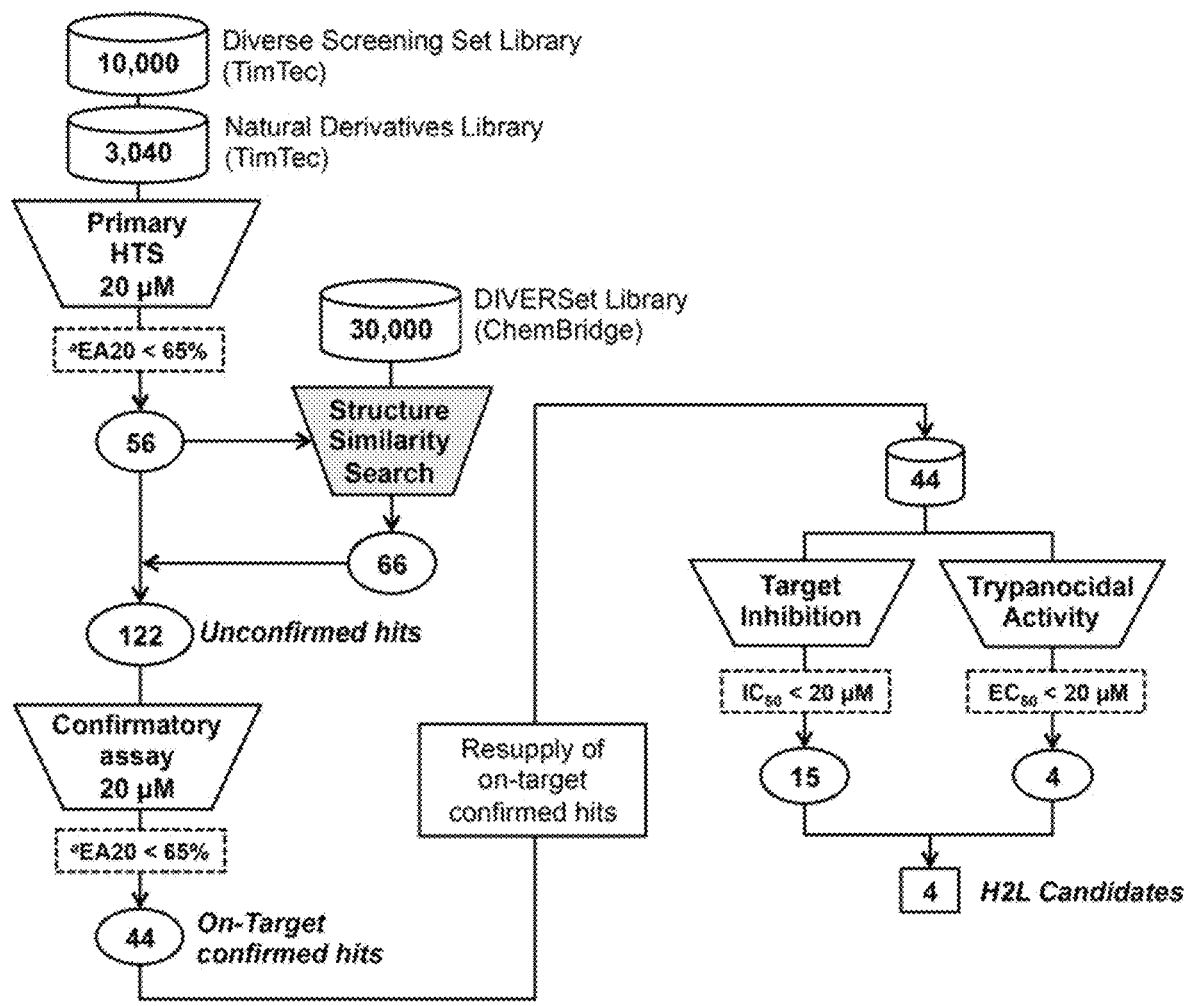
FIG. 2 is a flowchart representing the HTS scheme performed beginning with the initial screen of 13,040 compounds (from two libraries) against TcGlcK followed by structure searches from a library of 30,000 compounds. $^a$EA20 is enzyme activity at 20 μM compound concentration from the screening library.

Compound Libraries and Reagents for HTS:

The primary HTS of TcGlcK was carried out using the Diversity Screening Set library (10,000 compounds) and the Natural Derivatives library (3,040 compounds) of TimTec (Newark, Del.). Compounds having structural similarity to hits from the primary screen were used from the DIVERSet library of Chem Bridge (San Diego, Calif.). All libraries had compounds at an initial concentration of 10 mM in 100% DMSO but were transferred to 384 well-plates (daughter plates) by dilution to 1 mM using 100% DMSO. In these daughter plates, columns 1, 2, 23, and 24 were filled with only DMSO for the purpose of having positive/negative controls. Compounds selected for resupply were purchased from their corresponding supplier (i.e. TimTec or Chem Bridge).
Primary HTS Assay:

The TcGlcK assay was performed through its linking with the HsΔG6PDH-diaphorase enzyme-coupled assay system as schematically illustrated in FIG. 1. All of the compounds were tested in quadruplicate using the JANUS-MDT liquid handler equipped with a 384-tip head that was used to transfer 22 μL of a reagent mix [130 U/mL HsΔG6PDH, 100 mM NADP+, 1 kU/mL diaphorase, 10 mM resazurin, and 19 μM TcGlcK in a reaction buffer (see below)], 0.5 μL of 1 mM compounds in 100% DMSO (from the daughter plate, see above), and 2.5 μL of a substrate mix [4 mM D-glucose and 6 mM ATP in a reaction buffer] to a 384-well plate (total volume per well was 25 μL). The reaction buffer was 0.1 M triethanolamine (pH 8.5), 8.0 mM MgCl$_2$, and 0.01% (v/v) Triton X-100. The final assay concentrations (FACs) were 0.5 U/mL HsΔG6PDH, 100 μM NADP+, 1 U/mL diaphorase, 20 μM resazurin, 2.5 nM TcGlcK, 20 μM compounds (from the daughter plate, see above), 0.4 mM D-glucose, 0.6 mM ATP, 0.1 M triethanolamine (pH 8.5), 8 mM MgCl$_2$, and 0.01% (v/v) Triton X-100. Briefly, compounds tested had a final concentration of 20 μM, TcGlcK activity was observed after 1 hr incubation at room temperature where resorufin relative fluorescence correlated to a 1:1 stoichiometry of G6P product formation, and experimental conditions were optimized to allow for linearity of resorufin relative fluorescence vs. time during the reaction. The assay was carried out using 384-well, black, v-bottom microplates (Greiner Bio-One) with a final volume of 25 μL per well. Pipetting steps were performed with a liquid handler having a 384-tip head, JANUS-MDT from Perkin Elmer (Waltham, Mass.). Compounds that gave rise to TcGlcK enzyme activity in the presence of 20 μM compound (EA20) that results in less than 65%) were categorized as unconfirmed hits to proceed as candidates. The methodology is schematically illustrated in FIG. 2.
Confirmatory Assay and Compound Resupply.

In addition to the unconfirmed hits identified from the primary HTS assay, the program DataWarrior was used to identify more candidates from structure similarity searching through the DIVERSet Library containing 30,000 compounds, from Chem Bridge. All of these candidates from the 3 screening libraries proceeded to a confirmatory assay, in which two evaluations were made. First, the same assay used in the primary HTS assay was performed to re-confirm hits (see above). Second, the evaluation of the possible inhibition effect on the HsΔG6PDH—diaphorase system was performed. Inhibitor solutions of hit candidates from the 3 libraries were transferred to a separate 384-well plate (daughter plate). All of the compounds were tested in quadruplicate using the JANUS-MDT liquid handler equipped with a 384-tip head that was used to transfer 22 μL of a reagent mix [0.178 μM HsΔG6PDH, 100 mM NADP$^+$, 1 kU/mL diaphorase, and 10 mM resazurin], 0.5 µL of 1 mM compounds (from the daughter plate), and 2.5 µL of a substrate solution [6 mM G6P in the same reaction buffer (see above)] to a 384-well plate. The FACs were 0.5 U/mL HsΔG6PDH, 100 µM NADP+, 1 U/mL diaphorase, 20 µM resazurin, 20 µM compounds (from the daughter plate), 0.6 mM G6P, 0.1 M triethanolamine (pH 8.5), 8 mM $MgCl_2$, and 0.01% (v/v) Triton X-100. The reaction was monitored as the formation of resorufin appeared over time and calculated velocities were normalized by using controls. False-positives that showed an influence on the TcGlcK inhibition by inhibiting the HsΔG6PDH—diaphorase coupled system were excluded from consideration. Confirmed on-target hits were resupplied by purchasing the powder form from the corresponding supplier, pertaining to the screening library used.

Inhibition Studies of TcGlcK by Confirmed Hits.

Determination of the $IC_{50}$ values was performed by the TcGlcK—HsΔG6PDH—diaphorase coupled assay, in which reaction velocities were obtained at various concentrations of inhibitors. In 96-well plates, solutions of the inhibitors were prepared by serial dilution. Briefly, column 1 served as a control having an inhibitor concentration of zero; however, columns 2 through 12 on a given row had 11 different inhibitor concentrations from a serial dilution. Using the JANUS-MDT liquid handler with a 96-tip head, assay reactions were carried out in quadruplicate in a 384-well plate and the following components were transferred per well: 44 µL of a reagent mix [130 U/mL HsΔG6PDH, 100 mM $NADP^+$, 1 kU/mL diaphorase, 10 mM resazurin, and 19 µM TcGlcK in a reaction buffer (0.1 M triethanolamine (pH 8.5), 8.0 mM $MgCl_2$, and 0.01% (v/v) Triton X-100)], 1 uL of 1 mM compound solutions in 100% DMSO, and 5 µL of a substrate mix [4 mM D-glucose and 6 mM ATP in the same reaction buffer]. The Envision microplate reader (PerkinElmer) was used to monitor the formation of resorufin in the fluorescence mode ($\lambda_{ex}$=530 nm; $\lambda_{em}$=615 nm). Reaction velocities were measured and normalized by the controls. Values of IC50 were calculated using the GraphPad Prism 6.0 software from nonlinear regression of the data.

T. cruzi Viability Assays.

General methods for the in vitro preparation of cell cultures for mammalian cells and parasites as well as the treatment of the T. cruzi infective form (amastigotes and trypomastigotes) (Tulahuen strain) in NIH-3T3 fibroblasts with inhibitors in order to determine $IC_{50}$ values or $EC_{50}$ values has been previously described. NIH-3T3 fibroblast cells and LLC-MK2 cells were incubated in Dulbecco's modified Eagle's medium (DMEM) lacking phenol red and supplemented with 10% fetal bovine serum (FBS) and penicillin-streptomycin-L-glutamine (PSG) [100 U/mL penicillin, 0.1 mg/mL streptomycin, and 0.292 mg/mL L-glutamine] in an environment that was humidified in the presence of 5% $CO_2$ at 37° C. The concentration of D-glucose in DMEM was 4.5 g/L. T. cruzi parasites (Tulahuen strain) that express the β-galactosidase gene (clone C4) were continuously cultured through infection of LLC-MK2 cells every 5-6 days in DMEM lacking phenol red and supplemented with 2% FBS and 1% PSG in a humidified environment containing 5% $CO_2$ at 37° C. On days 5-7 trypomastigotes were harvested from the culture medium. This was accomplished by first centrifuging the culture medium at 2,500 rpm for 7 min and allowing the trypomastigote life-stage form of the parasite to swim from the cell pellet (LLC-MK2 cells) in a 3 hr period. Amastigotes lack the kind of mobility observed in trypomastigotes and this provides a method of separating the two life-stage forms. Trypomastigotes ($1\times10^7$ cells) were allowed to infect LLC-MK2 cells ($1\times10^6$ cells) that were plated on a 75 $cm^2$ culture flask and parasites were counted using a Neubauer Chamber. After 5-7 days from this LLC-MK2 infection, T. cruzi trypomastigotes were harvested by means of centrifugation at 2,500 rpm for 7 min followed by rinsing twice in DMEM lacking the phenol red and supplemented with 2% FBS and 1% PSG. Phenol red was excluded from the colorimetric assay since it causes interference by absorbing light at 590 nm. The trypomastigote cells were centrifuged and were set to incubate for 3-5 hr. In the interim, a 96-well microtiter plate had wells filled with 100 µL of NIH-3T3 fibroblasts ($5\times10^4$ cells/well) and the mammalian cells were allowed to incubate for 3 hr for the purpose of attachment. Inhibitors identified from the HTS campaign were prepared as 50 mM stock solutions in 100% DMSO, and for each inhibitor, working concentrations ranged from 0-50 µM. Amphotericin B was used as a positive control (prepared as a 270 µM stock solution) and had a working concentration of 4 µM; and, positive and negative controls were used for all 96-well plates used. Such controls included (a) fibroblasts and parasites, (b) fibroblasts lacking parasites, and (c) the culture medium only. After the trypomastigotes finished incubating for the allotted time, 100 µL of the trypomastigotes (5×104 cells) in DMEM lacking phenol red supplemented with 2% FBS and 1% PSG were transferred into each well followed by a 96 hr incubation and trypomastigotes transformed into amastigotes. For color development, 50 µL of substrate solution [500 µM chlorophenol red-6-D-galactoside (CPRG), 0.5% detergent NP40, and phosphate buffered saline (PBS)] was added per well and was allowed to incubate at 37° C. for 4 hr followed by measuring the absorbance at 590 nm using a Tecan Spectra Miniplate reader. Absorbance values were proportional to parasite cell viability, $IC_{50}$ determinations were carried out through the GraphPad Prism software, and measurements were performed in triplicate.

Results and Discussion

Figure 3:
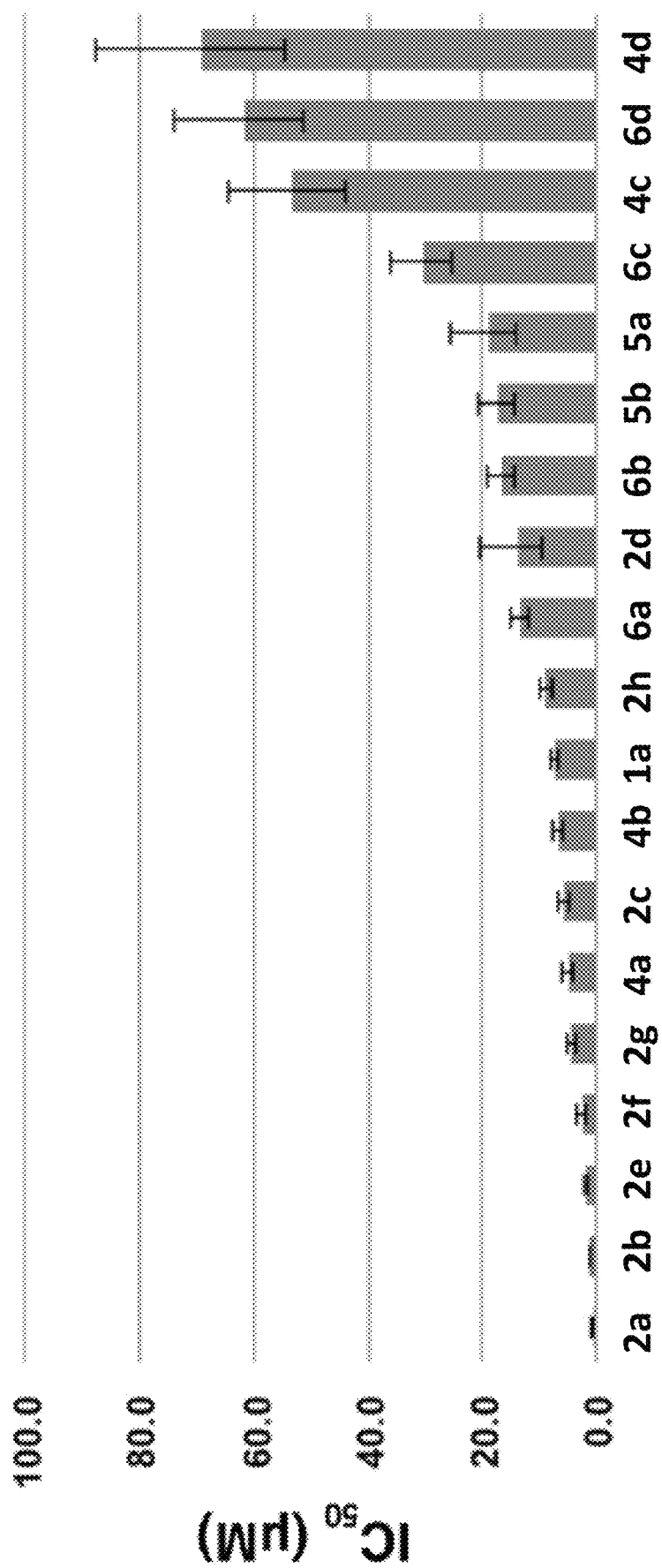
FIG. 3 graphically represents the activity of *T. cruzi* glucokinase inhibitors described herein. Inhibitor activity is represented by the mean $IC_{50}$ and error bars represent the standard error. $IC_{50}$ determinations were performed in triplicate.

The initial screening of 13,040 compounds against TcGlcK was performed in order to discover potential compound candidates. The HTS of these compounds (at a set compound concentration of 20 µM) resulted in 56 unconfirmed hits that lowered the enzyme activity to less than 65%. Structure searches were made against a much larger library of 30,000 compounds, in which an additional 66 compounds of interest were identified (as unconfirmed hits); this totaled 122 unconfirmed hits. A confirmatory assay procedure was carried out to remove false positives and resulted in 44 confirmed inhibitors of TcGlcK having the structures described above (i.e., compounds having the structures shown above as 1a-1n, 2a-2h, 3a-3c, 4a-4e, 5a-5c, 6a-6d, 7, 8, 9, 10, or 11). From these inhibitors, six scaffolds were identified as described above as Scaffolds 1-6 based on a core fragment search using the software DataWarrior and the remaining compounds were 5 singletons. The singletons include compounds having structures 7-11 illustrated above. The 44 confirmed inhibitors were tested for TcGlcK inhibition; however, only 19 compounds could successfully have an $IC_{50}$ determination performed. Fifteen of these compounds revealed an $IC_{50}$ value less than 20 µM (Table 1 and FIG. 3).

TABLE 1

| Structure ID | $IC_{50}$ (μM) | $R^2$ | 95% C.I. (+) | 95% C.I. (−) | Std. Error (+) | Std. Error (−) |
|---|---|---|---|---|---|---|
| 2a | 0.6 | 0.770 | 0.8 | 0.4 | 0.2 | 0.1 |
| 2b | 1.1 | 0.983 | 1.2 | 1.0 | 0.1 | 0.1 |
| 2e | 1.7 | 0.878 | 2.2 | 1.3 | 0.5 | 0.4 |
| 2f | 2.4 | 0.633 | 3.4 | 1.7 | 1.0 | 0.7 |
| 2g | 4.2 | 0.951 | 5.0 | 3.5 | 0.8 | 0.7 |
| 4a | 4.8 | 0.869 | 5.8 | 3.9 | 1.0 | 0.9 |
| 2c | 5.5 | 0.920 | 6.5 | 4.6 | 1.1 | 0.9 |
| 4b | 6.5 | 0.951 | 7.4 | 5.7 | 0.9 | 0.8 |
| 1a | 7.2 | 0.9985 | 8.0 | 6.5 | 0.8 | 0.7 |
| 2h | 8.7 | 0.959 | 9.9 | 7.6 | 1.2 | 1.1 |
| 6a | 13.2 | 0.972 | 15.1 | 11.6 | 1.8 | 1.6 |
| 2d | 13.7 | 0.874 | 20.2 | 9.3 | 6.5 | 44 |
| 6b | 16.5 | 0.959 | 19.1 | 14.3 | 2.6 | 2.3 |
| 5b | 17.1 | 0.827 | 20.8 | 14.0 | 3.7 | 3.0 |
| 5a | 18.8 | 0.432 | 25.3 | 13.9 | 6.5 | 4.8 |
| 6c | 30.2 | 0.938 | 36.2 | 25.3 | 5.9 | 5.0 |
| 4c | 53.2 | 0.802 | 64.4 | 43.9 | 11.3 | 9.3 |
| 6d | 61.6 | 0.914 | 73.9 | 51.3 | 12.3 | 10.2 |
| 4d | 69.1 | 0.802 | 87.4 | 54.7 | 18.3 | 14.5 |

Trypanocidal activity, presented as % viabile *T. cruzi* cells, was first assessed by a single-dose study, in which the concentration of the inhibitor compound was set to 80 μM and all 44 confirmed inhibitors (structures 1a-1n, 2a-2h, 3a-3d, 4a-4e, 5a-5c, 6a-6d, 7, 8, 9, 10, and 11) were tested separately against cell cultures of the *T. cruzi* infective form (both trypomastigote and amastigote life-stages) co-cultured in NIH-3T3 fibroblasts. Results are shown in Table 2, below. Compounds that reduced the survival rate to less than 50% progressed to $EC_{50}$ determinations. Active compounds reduced the viability to less than 25%; for moderately active hits, the remaining viable cells were between 25% and 75%; and for inactive hits, the viability was higher than 75%

TABLE 2

| Structure ID | % viability | Structure ID | % viability | Structure ID | % viability |
|---|---|---|---|---|---|
| 1c | 0.0 ± 0.0 | 3c | 0.0 ± 2.2 | 2b | 57.0 ± 2.8 |
| 4d | 0.0 ± 0.2 | 5a | 0.0 ± 3.3 | 2g | 62.8 ± 11.6 |
| 1g | 0.0 ± 0.4 | 1f | 0.0 ± 21.3 | 6d | 63.3 ± 0.4 |
| 5d | 0.0 ± 0.4 | 1a | 0.0 ± 24.2 | 2a | 66.5 ± 22.3 |
| 1k | 0.0 ± 0.6 | 1m | 0.6 ± 2.9 | 2f | 74.2 ± 5.3 |
| 1j | 0.0 ± 0.7 | 6b | 1.7 ± 2.7 | 2c | 79.0 ± 4.0 |
| 1b | 0.0 ± 0.8 | 1n | 2.4 ± 7.4 | 5c | 80.6 ± 3.9 |
| 4e | 0.0 ± 0.8 | 1i | 4.9 ± 4.7 | 2h | 81.2 ± 13.7 |
| 4a | 0.0 ± 1.0 | 6c | 20.4 ± 10.3 | 2i | 81.5 ± 11.3 |
| 1h | 0.0 ± 1.0 | 3a | 22.6 ± 5.7 | 7 | 84.3 ± 0.5 |
| 4c | 0.0 ± 1.0 | 11 | 34.6 ± 4.3 | 11 | 86.5 ± 0.9 |
| 1e | 0.0 ± 1.2 | 8 | 44.3 ± 5.1 | 5b | 87.1 ± 3.3 |
| 4b | 0.0 ± 1.2 | 10 | 50.5 ± 3.4 | 2e | 88.0 ± 9.4 |
| 1d | 0.0 ± 1.6 | 3b | 50.5 ± 12.4 | 2d | 88.7 ± 15.1 |
| 6a | 0.0 ± 1.8 | 9 | 52.7 ± 7.9 | — | — |

Four active hits were identified including compounds 4a, 4b, 1a, and 6a. These same compounds were also part of the 15 candidates from the TcGlcK—inhibition study described in FIG. 3 and Table 1. These four compounds contain scaffolds of three different core fragments, as follows: Scaffold 4—3-nitro-2-phenyl-2H-chromene for 4a and 4b; Scaffold 1—N-phenylbenzenesulfonamide for 1a; and Scaffold 6—Gossypol for 6a as described previously.

Figure 4:
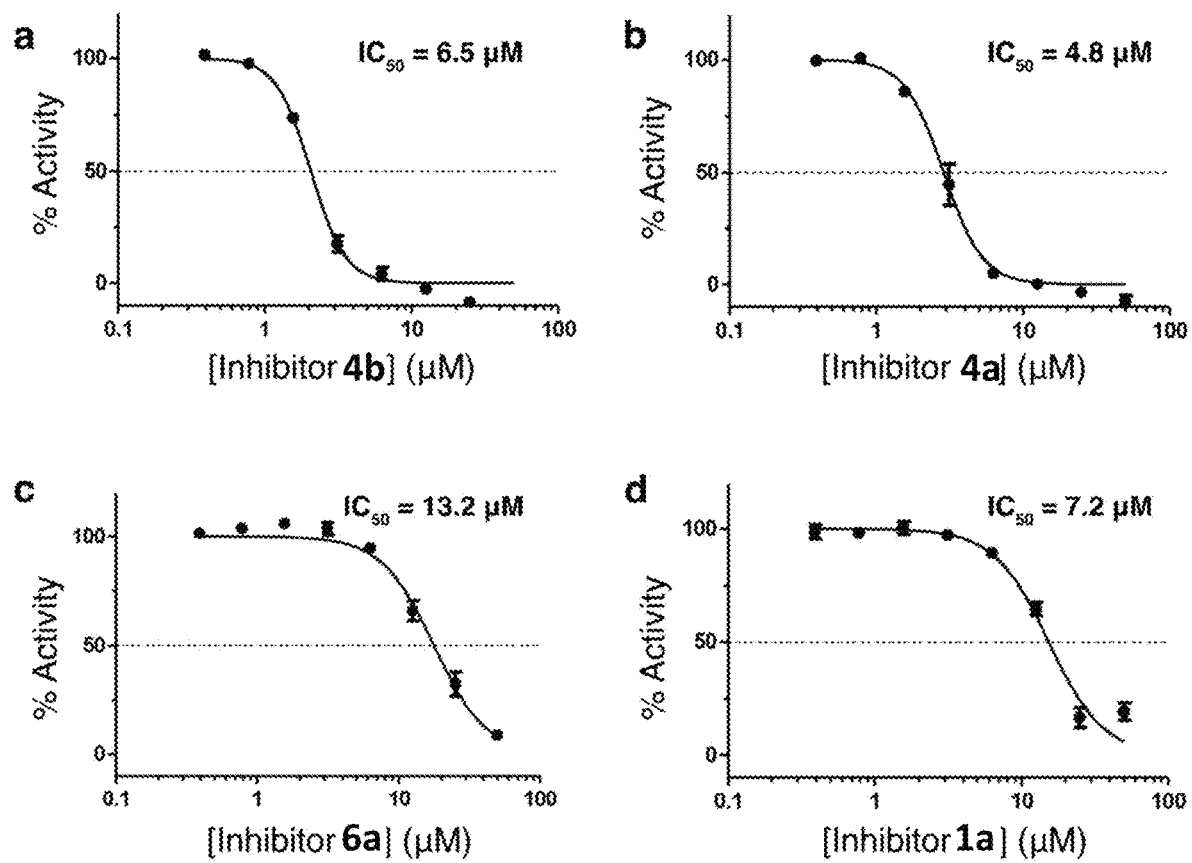
Figure 5:
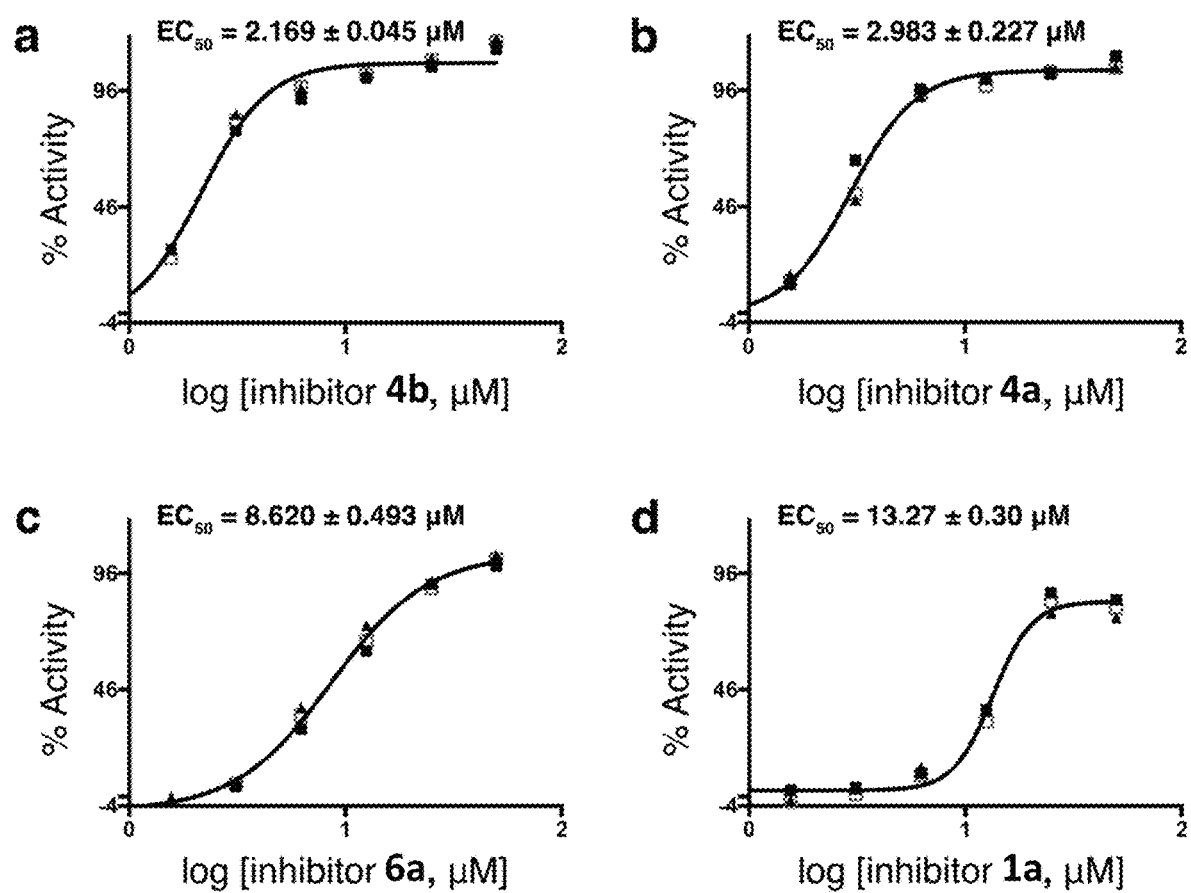

Results of TcGlcK—inhibition $IC_{50}$ curves are presented in FIG. 4 for compounds 4b (a), 4a (b), 6a (c), and 1a (d). Further testing of formal $EC_{50}$ in vitro experimentation using the *T. cruzi* infective form (amastigotes and trypomastigotes) co-cultured in NIH-3T3 fibroblasts was performed (Table 3 and FIG. 5). Compounds 4a and 4b showed very similar in vitro *T. cruzi* $EC_{50}$ values to that of benznidazole. By comparing the $IC_{50}$ values from enzyme—inhibitor interactions versus $EC_{50}$ values from in vitro studies of the four hit-to-lead compounds, a strong correlation exists and suggests that TcGlcK acts as a chemically validated drug-target for Chagas' disease.

TABLE 3

| Structure ID | [a]$EC_{50}$ (μM) | [b]$IC_{50}$ (μM) |
|---|---|---|
| 4b | 2.169 ± 0.045 | 6.5 |
| 4a | 2.983 ± 0.227 | 4.8 |
| 6a | 8.620 ± 0.493 | 13.2 |
| 1a | 13.27 ± 0.30 | 7.2 |

[a]In vitro *T. cruzi* (Tulahuen strain) intracellular infective form (amastigote and trypomastigote) growth inhibition in NIH-3T3 fibroblasts.
[b]Enzymatic assays: TcGlcK – Inhibitor $IC_{50}$ determinations.

Inhibition Studies of TcGlcK by the Hit-to-Lead Candidates.

Of these four candidates, three compounds (4a, 4b, and 6a) followed the Lipinski's Rule of Five (Ro5) criteria from their physiochemical properties (Table 4), in which each of their Lipinski scores had a value of 4. Compound 6a, which had a score of 1, was not found to be in agreement with the Ro5 criteria mainly because it is a natural product. Ro5 criteria included the following: (i) molecular weight (MW) ≤500 g/mol, (ii) CLogP≤5, (iii) number of H-bond donors≤5, and (iv) number of H-bond acceptors 10. Compounds 4a, 4b, and 1a were also in agreement with other important physiochemical parameters common to many excellent drugs, including: (i) polar surface area (PSA)<140 Å$^2$, (ii) molar refractivity (MR) ranging from 40-130 cm$^3$/mol, and (iii) the number of atoms in the molecule (including H atoms) ranging from 20-70 atoms. On the other hand, the gossypol compound 6a was not in agreement with these extended criteria. Compound 6a has a PSA of 347.96 Å$^2$ and 110 atoms in its molecular formula, values well over the common values.

TABLE 4

| Structure ID | Molec. Formula (no. atoms) | MW[a] (g/mol) | CLogP[b] | H-bond donor[b] | H-bond acceptor[b] | Lipinski Score[c] | MR[d,e] (cm$^3$/mol) | PSA (Å$^2$)[b] |
|---|---|---|---|---|---|---|---|---|
| 4b | $C_{18}H_{16}BrNO_5$ (41) | 406.23 | 3.4664 | 0 | 6 | 4 | ND | 73.51 |
| 4a | $C_{19}H_{17}Cl_2N\,O_5$ (44) | 410.25 | 4.3595 | 0 | 6 | 4 | ND | 73.51 |
| 6a | $C_{44}H_{46}N_8O_{10}S_2$ (110) | 911.03 | 2.0428 | 12 | 18 | 1 | ND | 347.96 |

TABLE 4-continued

| Structure ID | Molec. Formula (no. atoms) | MW[a] (g/mol) | CLogP[b] | H-bond donor[b] | H-bond acceptor[b] | Lipinski Score[c] | MR[d,e] (cm³/mol) | PSA (Å²)[b] |
|---|---|---|---|---|---|---|---|---|
| 1a | $C_{13}H_{10}BrCl_2NO_3S$ (31) | 411.10 | 3.8259 | 1 | 4 | 4 | 86.49 | 63.78 |

[a]MW is number average molecular weight; MR is molar refractivity; and PSA is polar surface area.
[b]Calculated using OSIRIS Datawarrior (version 4.6.1).
[c]Lipinski's Rule of Five; score is out of 4.
[d]Calculated using ChemDraw Ultra (version 12.0).
[e]ND: Not determined These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of inhibiting *T. cruzi* glucokinase and/or *T. cruzi* hexokinase in a human, comprising:
administering to a human infected with *T. cruzi* a pharmaceutical composition comprising a pharmaceutically acceptable carrier and a compound having the following structure:

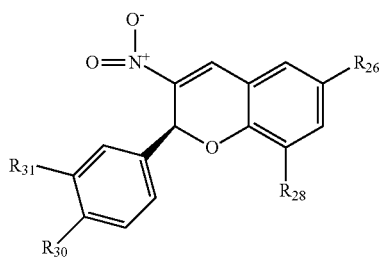

in which
$R_{26}$ is H, Br, or Cl,
$R_{28}$ is H or Cl,
$R_{30}$ is —OCH$_3$ or —OCH$_2$CH$_3$, and
$R_{31}$ is —OCH, or —OCH$_3$ or —OCH$_2$CH$_3$.

2. A method of treating a mammal that is infected by *T. cruzi*, the method comprising administering to the mammal a pharmaceutical composition comprising a pharmaceutically acceptable carrier and a compound having the following structure:

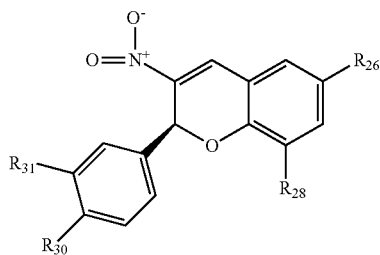

in which
$R_{26}$ is H, Br, or Cl,
$R_{28}$ is H or Cl,
$R_{30}$ is —OCH$_3$ or —OCH$_2$CH$_3$, and
$R_{31}$ is —OCH$_3$ or —OCH$_2$CH$_3$, wherein *T. cruzi* glucokinase and/or *T. cruzi* hexokinase are inhibited in the mammal.

3. The method of claim 1, wherein the compound has the following structure:

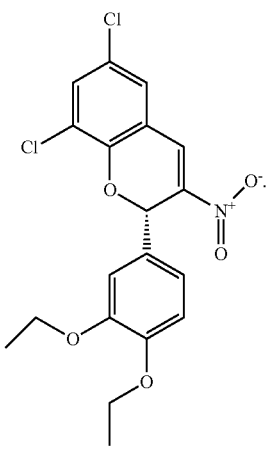

4. The method of claim 1, wherein the compound has the following structure:

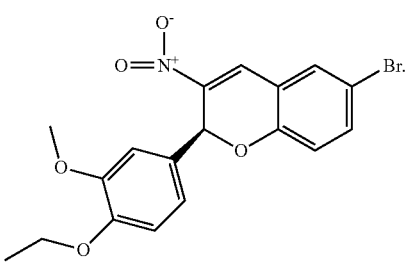

5. The method of claim 1, wherein the compound has the following structure:

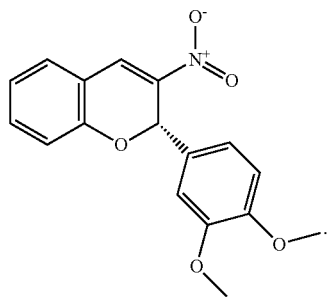

4c

6. The method of claim 1, wherein the compound has the following structure:

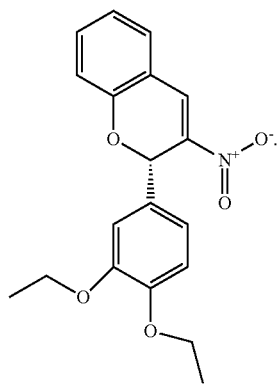

4d

7. The method of claim 2, wherein the compound has the following structure:

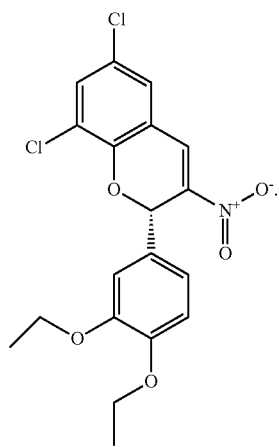

4a

8. The method of claim 2, wherein the compound has the following structure:

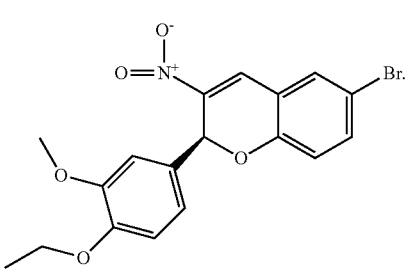

4b

9. The method of claim 2, wherein the compound has the following structure:

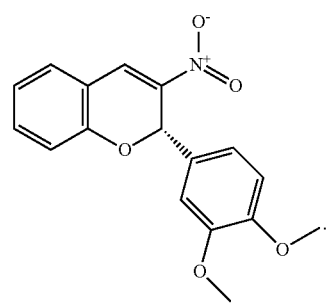

4c

10. The method of claim 2, wherein the compound has the following structure:

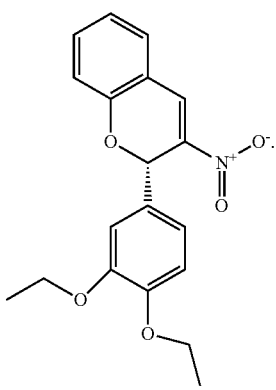

4d

* * * * *